United States Patent
Reuter et al.

(10) Patent No.: US 7,273,943 B2
(45) Date of Patent: Sep. 25, 2007

(54) PROCESS FOR THE PREPARATION OF HIGH-PURITY ZIRCONIUM, HAFNIUM, TANTALUM AND NIOBIUM ALKOXIDES

(75) Inventors: Knud Reuter, Krefeld (DE); Friedrich Zell, Rheinfelden (DE); Martina Ebner, Murg (DE)

(73) Assignee: H. C. Starck GmbH, Goslar (DE)

( * ) Notice: Subject to any disclaimer, the term of this patent is extended or adjusted under 35 U.S.C. 154(b) by 0 days.

(21) Appl. No.: 11/509,157

(22) Filed: Aug. 24, 2006

(65) Prior Publication Data

US 2007/0056468 A1    Mar. 15, 2007

(30) Foreign Application Priority Data

Aug. 27, 2005  (DE) .................. 10 2005 040 618
Nov. 3, 2005   (DE) .................. 10 2005 052 444

(51) Int. Cl.
  *C07F 7/28*   (2006.01)
  *C07F 9/00*   (2006.01)
  *C01B 25/00*  (2006.01)

(52) U.S. Cl. .................. 556/42; 556/54; 106/287.26

(58) Field of Classification Search .................. 556/42, 556/54; 106/287.26
See application file for complete search history.

(56) References Cited

U.S. PATENT DOCUMENTS 6,548,685 B2   4/2003   Zell

FOREIGN PATENT DOCUMENTS

| DE | 101 13 169 | 9/2002 |
| JP | 6-192148   | 7/1994 |
| JP | 10-036299  | 2/1998 |
| JP | 2002-161059| 6/2002 |

*Primary Examiner*—Porfirio Nazario-Gonzalez
(74) *Attorney, Agent, or Firm*—Connolly Bove Lodge & Hutz

(57) ABSTRACT

A novel process for the preparation of high-purity zirconium, hafnium, tantalum and niobium alkoxides (alcoholates), novel tantalum and niobium compounds and a process for their preparation are provided. The process comprises the steps of mixing crude metal alkoxides $M(OR)_x$ having a halogen impurity of at least 0.05 wt. %, with an alcohol ROH, in which R is a $C_1$-$C_{12}$-alkyl radical, and subsequently or simultaneously metering in an excess of ammonia, based on the amount of mononuclear or polynuclear halogen-containing metal alkoxides.

14 Claims, No Drawings

PROCESS FOR THE PREPARATION OF HIGH-PURITY ZIRCONIUM, HAFNIUM, TANTALUM AND NIOBIUM ALKOXIDES

CROSS-REFERENCE TO RELATED APPLICATION

This application claims priority under 35 U.S.C. §119(a-e) to German application DE 10 2005 052444, filed Nov. 3, 2005 and German application DE 10 2005 040618, filed Aug. 27, 2005.

FIELD OF THE INVENTION

The invention relates to a novel process for the preparation of high-purity zirconium, hafnium, tantalum and niobium alkoxides (alcoholates), to novel tantalum and niobium compounds and to a process for their preparation.

BACKGROUND OF THE INVENTION

Zirconium, hafnium, tantalum and niobium alkoxides (alcoholates) can be used for the deposition of corresponding metal oxide layers by means of Chemical Vapour Deposition (CVD) and are therefore valuable starting compounds for the production of extremely resistant components used e.g. in the electronics industry. Such metal oxide layers can also be produced from the corresponding zirconium, hafnium, tantalum or niobium alkoxides via hydrolysis by the sol-gel method. The very high dielectric constant makes it possible e.g. to use zirconium, hafnium and tantalum oxide layers in so-called DRAMs (Dynamic Random Access Read/Write Memories).

However, a problem in the electronics industry is the extreme demands made on the purity of the starting materials for such layers, i.e. the alkoxides, so there is no lack of e.g. descriptions in the patent literature for special processes for the purification of niobium and tantalum alkoxides.

The most common, technically simplest and most economic preparation of zirconium, hafnium, niobium and tantalum alkoxides is based on the corresponding metal chlorides and alcohols. A comprehensive survey is given in the book "Alkoxo and Aryloxo Derivatives of Metals" by D. C. Bradley, R. C. Mehrotra, I. P. Rothwell and A. Singh, Academic Press, 2001. A typical procedure is described e.g. in DE 10113169 A1.

Preparation from the metal chlorides inevitably produces chloride as one of the main impurities that have to be separated from the alkoxides. The Cl content of crude tantalum ethoxide prior to distillation is thus around 500-1000 ppm or more. For example, crude products prepared according to DE 10113169 A1 typically contain over 3000 ppm of Cl.

The removal of chloride is therefore also the most frequently cited subject of the invention in the aforementioned patent for the purification of Ta and Nb alkoxides. This is due in particular to the fact that distillation alone is a process of only limited suitability. For example, experience has shown that a simple high-vacuum distillation of crude tantalum ethoxide only reduces the Cl content to about half. Better results are achieved by distillation over packed columns. However, because of the high boiling point of most alkoxides, e.g. tantalum. ethoxide, even at low pressure, this method entails considerable expenditure in terms of time and energy and the technically expensive production of an operating pressure of <1 mbar. The separation effect of a single distillation is usually insufficient, so a rather uneconomic multiple column distillation is required. These difficulties also arise in the removal of Cl from zirconium and hafnium alkoxides.

The Applicants of JP 2002161059 A2 attempt to solve this problem by aftertreating the crude tantalum ethoxide (containing e.g. 450 ppm of Cl) with ethanolic alkali metal hydroxide solution, especially NaOH solution. Although this method reduces the Cl content to the desired low range, experience has shown that contact between the tantalum ethoxide and alkali metal compounds in such operations leads to unwanted high alkali metal contents in the product, despite distillation.

A similar procedure is proposed in JP 06220069 A2, which uses alkali metal hydrides (e.g. LiH) or complex compounds of these hydrides. This again gives rise to the problem of additional contamination of the tantalum alkoxides with alkali metal ions.

The method used in JP 06192148 A2 is no different. The alkali metal or alkaline earth metal alkoxides used here, e.g. lithium or sodium ethoxide, likewise reduce the Cl content in the desired manner, but once again there are unwanted high alkali metal ion concentrations in the product. For example, when sodium ethoxide is added to tantalum ethoxide, the Na value typically rises from <1 ppm to 2-4 ppm, despite subsequent distillation.

Finally, JP 10036299 A2 also indicates an aftertreatment with alkali metal or alkaline earth metal compounds, in this case using carbonates. The effects of the alkali metal or alkaline earth metal contaminations on the products substantially freed of Cl are once again disadvantageous, in the same sense as in the patent applications cited above. The silver carbonate also proposed in said patent application is disadvantageous on economic grounds alone.

In all the cited patent applications, basic alkali metal and alkaline earth metal compounds are used for the purification. This is obviously based on the fact that, in the technically conventional methods of preparing tantalum and niobium alkoxides, the use of ammonia as an auxiliary base for the reaction of metal pentahalides with alcohols does not afford or allow products containing less than e.g. 100 ppm of Cl without additional aftertreatment and purification steps, including expensive distillations. Thus the teaching of the state of the art is that the use of ammonia as auxiliary base in the reaction of tantalum or niobium chloride with alcohols gives crude products that always contain more than 100 ppm of Cl, and usually many times this amount, prior to further purification by distillation.

SUMMARY OF THE INVENTION

The object of the present invention is therefore to provide a process which makes it possible, without the use of alkali metal or alkaline earth metal compounds, to prepare zirconium, hafnium, tantalum and niobium alkoxide crude products that contain less than 200, especially less than 100 and preferably less than 50 ppm of Cl before they are purified further by distillation. Such a process therefore makes it possible to combine products low in Cl and to the greatest possible extent free of alkali with a low distillation cost, which has been technically impossible hitherto.

Surprisingly, it has been found that, contrary to the teaching of the state of the art, it is possible to provide zirconium, hafnium, tantalum and niobium alkoxides with halogen contents, especially Cl contents, of less than 200, especially of less than 100 and preferably of less than 50 ppm, prior to their subsequent distillation, by using alcohols and ammonia under appropriate, specially chosen conditions.

The invention provides a process for the preparation of high-purity metal alkoxides $M(OR)_x$, in which M is Nb, Ta, Zr or Hf, preferably Nb or Ta, x is 5 in the case of M=Nb or Ta and 4 in the case of M=Zr or Hf, and R independently of one another are identical or different $C_1$-$C_{12}$-alkyl radicals, characterized in that crude metal alkoxides $M(OR)_x$ with a halogen content, especially Cl content, of >100 ppm, optionally of >200 ppm, containing as impurity at least 0.05 wt. %, preferably 0.1 to 10.0 wt. %, of mononuclear or polynuclear halogen-containing metal alkoxides, are mixed with at most 30 wt. %, preferably 4 to 12 wt. %, based on the total amount of crude alkoxide, of an alcohol ROH, in which R is a $C_1$-$C_{12}$-alkyl radical, and subsequently or simultaneously (e.g. after prior dissolution in the alcohol ROH), an excess of ammonia, based on the amount of mononuclear or polynuclear halogen-containing metal alkoxides, preferably of 0.1 to 5.0 wt. %, based on the total amount of crude alkoxide, is metered in.

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all sub-ranges subsumed therein.

Preferably, in the process, the radical R is $C_1$-$C_5$-alkyl and Hal is Cl. Particularly preferably, in the process, the radical R is $C_1$-$C_5$-alkyl, Hal is Cl and M is Ta. A very particularly preferred process is that in which, in the compound of formula (I), M is Ta, R is ethyl and Hal is Cl.

An essential aspect of this purification operation in the case of tantalum and niobium alkoxides is the origin of the major part of the analytically detected halide, preferably Cl, from the presence of the following compound, not described in the literature hitherto, in the crude product mixture:

$$M_2(OR)_9Hal \qquad (I).$$

M is niobium or tantalum, R is a $C_1$- to $C_{12}$-alkyl group and Hal is a halogen from the group comprising F, Cl, Br and I, preferably Cl.

Likewise, the origin of the major part of the analytically detected halide, preferably Cl, in crude zirconium and hafnium alkoxides is attributable to the presence of the following, possibly complex compounds in the crude product mixture:

$$M_p(OR)_{4p-q}Hal_q \qquad (II),$$

in which q=1, 2, 3 or 4, principally 1 or 2, and, because of the molecular complexity of the zirconium and hafnium alkoxides, p>1 and in fact is 2, 3 or 4, principally 3 or 4, except possibly for specific branched, preferably tertiary alkoxides. For the complexity of Zr and Hf alkoxides, i.e. the presence of oligomeric clusters, cf., for example, "Alkoxo and Aryloxo Derivatives of Metals" by D. C. Bradley, R. C. Mehrotra, I. P. Rothwell and A. Singh, Academic Press, 2001. Here M is zirconium or hafnium, R is a $C_1$- to $C_{12}$-alkyl group and Hal is a halogen from the group comprising F, Cl, Br and I, preferably Cl.

Thus the mononuclear or polynuclear halogen-containing metal alkoxides removed from the crude alkoxides by means of the process according to the invention are essentially the dinuclear halogen-containing compound of the formula $M_2(OR)_9Hal$ in the case of M=Nb or Ta and essentially one or more polynuclear complex halogen-containing compounds of the formula $M_p(OR)_{4p-q}Hal_q$ in the case of M=Zr or Hf.

Particularly in the case of specific branched, especially tertiary alkyl radicals R, it is also possible, both for zirconium and hafnium alkoxides and for tantalum and niobium alkoxides, for mononuclear halogen-containing metal alkoxides, i.e. compounds of general formula (II) in which p is 1, to be present as impurities in the crude product mixture.

Within the framework of the invention, $C_1$-$C_{12}$-alkyl is e.g. methyl, ethyl, n-propyl, isopropyl, n-butyl, sec-butyl, tert-butyl, n-pentyl, 1-methylbutyl, 2-methylbutyl, 3-methylbutyl, neopentyl, 1-ethylpropyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl and n-dodecyl.

Preferred $C_1$-$C_5$-alkyl radicals are especially those belonging to the group comprising methyl, ethyl, n-propyl, isopropyl, n-butyl, sec-butyl and n-pentyl, ethyl, n-propyl, n-butyl and n-pentyl are particularly preferred.

Examples of suitable compounds that can preferably be purified are tantalum methoxide, tantalum ethoxide, tantalum n-propoxide, tantalum 2-propoxide, tantalum n-butoxide, tantalum 2-butoxide (=tantalum sec-butoxide), tantalum isobutoxide (=tantalum 2-methyl-1-propoxide), tantalum tert-butoxide, tantalum n-pentoxide and the corresponding niobium compounds. Tantalum ethoxide, tantalum n-propoxide, tantalum n-butoxide and tantalum n-pentoxide are particularly preferred.

Apart from the compounds $M(OR)_x$ and ROH present in the mixture and contaminated by $M_2(OR)_9Hal$ or $M_p(OR)_{4p-q}Hal_q$, inert solvents, i.e. solvents that do not react with the metal compounds, can additionally be used in the novel process. Examples of such solvents are linear, branched or cyclic aliphatic hydrocarbons such as n-pentane, n-hexane, n-heptane, isooctane or cyclohexane, or aromatic hydrocarbons such as toluene or xylene, or mixtures of such solvents. Typically, the proportion by weight of these solvents that are additionally used does not exceed the amount by weight of metal compounds.

The synthesis steps which have led to the above-mentioned crude metal oxides are irrelevant to the purification process according to the invention, although a synthesis from metal halides $MHal_5$ must always have taken place. Such syntheses are frequently described in the literature and patent literature; cf., for example, "Alkoxo and Aryloxo Derivatives of Metals" by D. C. Bradley, R. C. Mehrotra, I. P. Rothwell and A. Singh, Academic Press, 2001. The process according to the invention does not apply to the purification of crude metal alkoxides prepared by processes other than from $MHal_5$ and ROH, e.g. from metal amides or amide-imides and ROH, or e.g. by electrolysis of the metals M in alcohols ROH.

The alkoxides reacted with ammonia/ROH as described above are worked up by filtration of the ammonium halide formed and removal of all the solvents by distillation, e.g. under reduced pressure. It is advantageous here, although not obligatory, to remove the alcohol ROH used by distillation—preferably under reduced pressure—before the filtration. If this removal is carried out, it is important to choose a lower temperature preferably of <40° C. At higher temperatures, especially at 80-100° C. and above, a reaction of the metal alkoxide takes place according to the equation below (shown in detail using tantalum and niobium alkoxides as examples) due to the concentration of HHal that exists in equilibrium when ammonium halide is present; for the sake of clarity, said equation has been formulated for the dimeric alkoxides that are usually present in reality rather than the "pentaalkoxides" $M(OR)_5$ referred to by way of simplification:

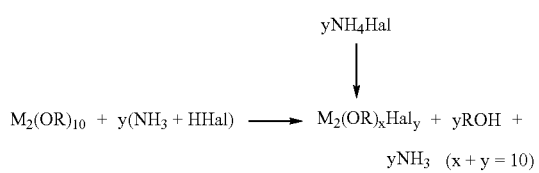

$$yNH_3 \quad (x+y=10)$$

For non-dimerizing metal alkoxides for which molecules $M(OR)_5$ do actually exist, the equation shall be formulated analogously as follows:

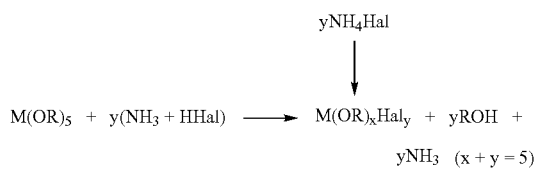

$$yNH_3 \quad (x+y=5)$$

The halogen content of the product to be purified is again increased by this reaction at elevated temperatures, so the success of the purification operation with $NH_3/ROH$ would be negated.

Similar reactions can be formulated by analogy for the zirconium and hafnium alkoxides $M(OR)_4$.

Also advantageous is a preferred variant in which the mixture obtained after the reaction with $NH_3/ROH$ is treated, before or after the removal of ROH by distillation, with an aliphatic hydrocarbon (HC) such as n-pentane, n-hexane, n-heptane, isooctane or cyclohexane, or an aromatic HC, e.g. toluene or xylene, and then filtered. The amount of HC added here can be varied within wide limits; amounts by weight of 20 to 200%, based on the amount of crude alkoxide, are particularly advantageous.

Thus the novel process has various preferred variants of the work-up following the reaction of the crude alkoxide with $NH_3/ROH$:
1) Filtration, then removal of ROH by distillation.
2) Removal of ROH by distillation, then filtration.
3) Filtration, removal of ROH by distillation, addition of HC, filtration.
4) Removal of ROH by distillation, addition of HC, filtration.
5) Addition of HC, filtration, removal of HC/ROH by distillation.

There are yet more conceivable sequences of filtration/removal of ROH/addition of HC which can be implemented. Variants 3) and 4) are particularly advantageous for the purity of the product.

The purification of the crude alkoxides according to the invention is conventionally followed by a distillation. It is a particular advantage of the invention that this distillation now no longer requires a large separation effect, i.e. a packed column or a distillation apparatus of comparable separation effect, and only has to be carried out once to obtain an alkoxide containing less than 200, especially less than 100 and preferably less than 50 ppm of Hal. The invention. thus improves the economics of the metal alkoxide preparation considerably by making savings in terms of time, energy and equipment.

The invention also provides the compounds $M_2(OR)_9Hal$, not hitherto described in the literature, as well as mixtures of $M(OR)_5$ and at least 0.05 wt. % of $M_2(OR)_9Hal$ and preferably 0.1 to 10 wt. % of $M_2(OR)_9Hal$, in which M is Ta or Nb.

Preferred compounds or corresponding mixtures are those in which $R=C_1-C_5$-alkyl and Hal=Cl. Particularly preferred compounds are tantalum compounds and mixtures thereof in which $R=C_1-C_5$-alkyl and Hal=Cl. Very particularly preferred compounds are those in which M=Ta, R=ethyl and Hal=Cl.

The compounds $M_2(OR)_9Hal$ can be prepared e.g. by reacting metal alkoxides $M(OR)_5$ or $M_2(OR)_{10}$ in the appropriate stoichiometric ratio with halides $MHal_5$ ("comproportionation"). This comproportionation reaction can be carried out with a solvent or, preferably, without a solvent at an elevated temperature preferably of 40 to 120° C. A possible alternative for the preparation of these compounds is to react the metal alkoxides with acetyl halides in a molar ratio of 2:1, e.g. with acetyl chloride in the case where Hal=Cl.

These novel compounds can be used e.g. as educts for secondary compounds formed by replacement of the Hal with suitable nucleophiles, e.g. optionally substituted amino groups, alkyl groups, alkylthio groups or other alkoxy groups.

The comproportionation is also suitable for the preparation of more highly halogenated, mixed metal alkoxide-halides, e.g. $M(OR)_4Hal$ or $M_2(OR)_8Hal_2$.

The Examples which follow serve to illustrate the invention by way of example without implying a limitation.

EXAMPLES

Example 1

Purification of Crude Tantalum Ethoxide

Initial Weights:

2992 g crude undistilled tantalum ethoxide prepared according to DE 10113169

A1

299 g ethanol abs.

15.55 g ammonia, gaseous (gas.) and anhydrous (anh.)

Tantalum ethoxide (3500 ppm of Cl) and ethanol were placed in the reaction vessel; at RT and without cooling, ammonia was introduced over 2 h, with stirring (exothermic up to approx. 30° C.). The reaction mixture was stirred for a further 2 h at RT. After standing overnight, ethanol was stripped off at max. 40° C. under a water-jet vacuum and finally under a high vacuum of <1 mbar. 1500 ml of hexane were then added and the mixture was filtered on a fluted filter. Hexane was then removed at 16 mbar/80° C. and finally at <1 mbar/80° C.

Cl (by colorimetry): 25 ppm.

Example 2

Preparation of Tantalum Ethoxide and Purification 53.8 g (150 mmol) of tantalum chloride were suspended in 30 ml of dry heptane. 500 ml (853 mmol) of abs. ethanol were metered in over ½ h, the internal temperature being kept below 30° C. by cooling with water/ice and the ethanol being slowly added dropwise in the initial phase in order to reduce the exothermicity. The mixture was subsequently stirred for ½ h at 25° C.

24.94 g (1.464 mol) of ammonia were then introduced over 1.5 h at max. 30° C. (cooling with water/ice). After standing overnight, the ammonium chloride was filtered off and ethanol was distilled off at 20 mbar and finally under a high vacuum of <1 mbar.

4.3 g of abs. ethanol were added to 42.9 g of the crude ethoxide obtained, and 2.07 g (121 mmol) of ammonia were then introduced over 1 h at RT. After stirring for a further 1.5 h at 23° C., ethanol was stripped off at <40° C., 40 ml of hexane were added and the mixture was filtered. The hexane was then distilled off at 20 mbar/<40° C. Cl (by colorimetry): 33 ppm.

Example 3

Preparation of Niobium Ethoxide and Purification 40.5 g (150 mmol) of niobium chloride were suspended in 30 ml of dry heptane. 550 g of abs. ethanol were metered in over ½ h, the internal temperature being kept below 40° C. by cooling with water/ice and the ethanol being slowly added dropwise in the initial phase in order to reduce the exothermicity. The mixture was subsequently stirred for ½ h at 25° C.

16.61 g (975 mmol) of ammonia were then introduced over 1.5 h at max. 35° C. (cooling with water/ice). The ammonium chloride was then filtered off and ethanol was distilled off at 20 mbar and finally under a high vacuum of <1 mbar.

3.5 g of abs. ethanol were added to the crude ethoxide obtained, and 1.69 g (992 mmol) of ammonia were then introduced over ½ h at 23° C. After stirring for a further 2 h at 23° C., 40 ml of hexane were added, the mixture was filtered and the ammonium chloride on the filter was rinsed with hexane. The hexane solutions were distilled; the niobium ethoxide obtained after distillation of the hexane contained approx. 40 ppm of Cl. After distillation at 160°/0.49 mbar, 35.9 g (=75% of theory) of niobium ethoxide were obtained. Cl (by colorimetry): 20 ppm.

Example 4

Preparation of $Ta_2(OEt)_9Cl$ from Tantalum Ethoxide and Tantalum Chloride 3.58 g (10 mmol) of tantalum chloride and 36.56 g (90 mmol) of tantalum ethoxide were mixed and heated at 80° C. for 7 h, with stirring. After cooling, a liquid product was obtained with a small amount of solids at the bottom. The liquid phase was decanted off (approx. 3 g) and consisted of $Ta_2(OEt)_9Cl$.

$^1$H NMR ($C_6D_6$, 400 MHz, δ rel. to TMS): 1.24 (t, J=6.85 Hz); 1.32 (t, J=6.85 Hz); 1.44 (t, J=6.85 Hz); 4.62 (m, br); 4.85 (m, br).

Elemental analysis %: C, 26.9; H, 5.65; Cl, 4.42; $C_{18}H_{45}ClO_9Ta_2$: C, 27.1; H, 5.9; Cl, 4.32.

Example 5

Preparation of $Ta_2(OEt)_9Cl$ from Tantalum Ethoxide and Acetyl Chloride 40.62 g (100 mmol) of tantalum ethoxide were placed in 100 ml of dry toluene. 3.92 g (50 mmol) of acetyl chloride were added dropwise and the mixture was refluxed for 1 h. All the volatile constituents were then distilled off up to 30° C./0.5 mbar. The liquid residue was decanted from a small amount of solids and consisted of $Ta_2(OEt)_9Cl$.

$^1$H NMR ($C_6D_6$, 400 MHz, δ rel. to TMS, ppm): 1.24 (t, J=6.85 Hz); 1.31 (t, J=6.85 Hz); 1.44 (t, J=6.85 Hz); 4.62 (m, br); 4.84 (m, br).

Example 6

Preparation of $Ta(OEt)_4Cl$ According to the Literature: Kapoor, R. N.; Prakash, Sarla; Kapoor, P. N. Indian Journal of Chemistry (1967), 5 (9), 442-3 (Comparative Example to verify the different identity from $Ta_2(OEt)_9Cl$, not according to the invention)

20.3 g (50 mmol) of tantalum ethoxide were placed in 100 ml of dry toluene. 3.92 g (50 mmol) of acetyl chloride were added dropwise and the mixture was refluxed for 1 h. All the volatile constituents were then distilled off up to 30° C./0.5 mbar. White waxy residue: $Ta(OEt)_4Cl$.

M.p.: 61-65° C.

$^1$H NMR ($C_6D_6$, 400 MHz, δ rel. to TMS, ppm): 1.21 (12H, t, J=6.85 Hz); 1.30 (6H, t, br); 1.48 (6H, t, J=6.85 Hz); 4.59 (4H, m, br); 4.74 (4H, m, J=6.85 Hz); 4.85 (8H, m, br).

Elemental analysis %: C, 22.7; H, 4.53; Cl, 9.15; $C_8H_{20}ClO_4Ta$: C, 24.2; H, 5.08; Cl, 8.94.

Example 7

Preparation of $Ta(OEt)_4Cl$ by Comproportionation (to Verify the Different Identity from $Ta_2(OEt)_9Cl$, not According to the Invention)

11.02 g (30.8 mmol) of tantalum chloride and 50.00 g (123 mmol) of tantalum ethoxide were mixed and heated at 80° C. for 6 h, with stirring. After cooling, a uniform, white waxy product was obtained.

M.p.: 65° C.

$^1$H NMR ($C_6D_6$, 400 MHz, δ rel. to TMS, ppm): 1.21 (12H, t, J=6.85 Hz); 1.30 (6H, t, br); 1.48 (6H, t, J=6.85 Hz); 4.59 (4H, m, br); 4.74 (4H, m, J=6.85 Hz); 4.85 (8H, m, br).

Example 8

Purification of Crude Hafnium Ethoxide

Initial Weights:

25 g crude undistilled hafnium ethoxide prepared from $HfCl_4$ according to DE 10113169A1

2 g ethanol abs.

38 ml hexane 1.5 g ammonia, gaseous and anhydrous

Hafnium ethoxide (>1000 ppm of Cl), ethanol and hexane were placed in the reaction vessel; at RT and without cooling, ammonia was introduced over 35 min, with stirring. The reaction mixture was subsequently stirred for a further 2¼ h at RT. About 7.5 g of ethanol/hexane mixture were then stripped off under a water-jet vacuum at max. 40° C. 19 ml of hexane were then added and the mixture was filtered on a fluted filter. Hexane was then removed at 16 mbar/80° C. and finally at <1 mbar/70° C.

Cl (by colorimetry): 128 ppm.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the preparation of high-purity metal alkoxides $M(OR)_x$, in which M is Nb, Ta, Zr or Hf, x is 5 in the case of M=Nb or Ta and 4 in the case of M=Zr or Hf, and R independently of one another are identical or different $C_1$-$C_{12}$-alkyl radicals, wherein
    (a) a crude metal alkoxide product $M(OR)_x$ with a halogen content of >200 ppm, containing as impurity at least 0.05 wt. % of mononuclear or polynuclear halogen-containing metal alkoxides, is mixed with
    (b) at most 30 wt. % based on the total amount of crude alkoxide, of an alcohol ROH, in which R is a $C_1$-$C_{12}$-alkyl radical, and
    (c) subsequently or simultaneously an excess of ammonia, based on the amount of mononuclear or polynuclear halogen-containing metal alkoxides, based on the total amount of crude alkoxide, is metered in.

2. Process according to claim 1, wherein M is Ta or Nb and the mononuclear or polynuclear halogen-containing metal alkoxide present as impurity is the compound $M_2(OR)_9Hal$, in which Hal is F, Cl, Br or I and R is as defined in claim 1.

3. Process according to claim 1, wherein M is Zr or Hf and the mononuclear or polynuclear halogen-containing metal alkoxide(s) present as impurity is (are) at least one compound $M_p(OR)_{4p-q}Hal_q$, in which Hal is F, Cl, Br or I, q is 1, 2, 3 or 4, p is 2, 3 or 4 and R is as defined in claim 1.

4. Process according to claim 1, wherein the radical R is $C_1$-$C_5$-alkyl and Hal is Cl.

5. Process according to claim 1, wherein the radical OR is an ethoxy group and M is Ta.

6. A compound of the formula $M_2(OR)_9Hal$ in which R is as defined in claim 1, M is Ta or Nb and Hal is a halogen from the group comprising F, Cl, Br and I.

7. A compound of the formula $M_2(OR)_9Hal$ according to claim 6 in which R is a $C_1$-$C_5$-alkyl radical and Hal is Cl.

8. A compound according to claim 7, wherein it is $Ta_2(OEt)_9Cl$.

9. Mixtures of compounds $M_2(OR)_9Hal$ according to claim 6 and $M(OR)_5$ containing at least 0.05 wt. % of $M_2(OR)_9Hal$.

10. Mixtures according to claim 9 in which R is a $C_1$-$C_5$-alkyl radical and Hal is Cl.

11. Mixtures according to claim 9 consisting of $Ta_2(OEt)_9Cl$ and $Ta(OEt)_5$.

12. Process according to claim 1, wherein the halogen content is from 0.1 to 10.0 wt. %.

13. Process according to claim 1, wherein the amount of alcohol ROH is from 4 to 12 wt. %.

14. Process according to claim 1, wherein the amount of ammonia is between 0.1 to 5.0 wt. %.

* * * * *